US011244766B2

(12) United States Patent
Downs et al.

(10) Patent No.: US 11,244,766 B2
(45) Date of Patent: *Feb. 8, 2022

(54) SYSTEMS AND METHODS FOR STORING, PROCESSING AND UTILIZING PROPRIETARY GENETIC INFORMATION

(71) Applicant: YouGene, Inc., New York, NY (US)

(72) Inventors: Ryan Downs, Alexandria, VA (US); Ferdinand Los, Rotterdam (NL); Orhan Soykan, Shoreview, MN (US); Roger C. Hahn, Fairfax, VA (US)

(73) Assignee: YOUGENE, CORP., New York, NY (US)

( * ) Notice: Subject to any disclaimer, the term of this patent is extended or adjusted under 35 U.S.C. 154(b) by 167 days.

This patent is subject to a terminal disclaimer.

(21) Appl. No.: 16/128,472

(22) Filed: Sep. 11, 2018

(65) Prior Publication Data

US 2019/0013104 A1 Jan. 10, 2019

Related U.S. Application Data

(63) Continuation of application No. 14/483,921, filed on Sep. 11, 2014, now Pat. No. 10,102,927, which is a continuation-in-part of application No. 13/371,422, filed on Feb. 11, 2012, now abandoned, and a continuation-in-part of application No. 14/452,979, filed on Aug. 6, 2014, now abandoned.

(51) Int. Cl.
| | |
|---|---|
| *G06Q 20/06* | (2012.01) |
| *G16H 15/00* | (2018.01) |
| *G16H 50/70* | (2018.01) |
| *G06Q 50/18* | (2012.01) |
| *G16H 50/30* | (2018.01) |
| *G16H 10/60* | (2018.01) |
| *G16B 20/00* | (2019.01) |
| *G16B 50/00* | (2019.01) |
| *G16B 20/20* | (2019.01) |

(52) U.S. Cl.
CPC .......... *G16H 50/70* (2018.01); *G06Q 50/184* (2013.01); *G16B 20/00* (2019.02); *G16B 20/20* (2019.02); *G16B 50/00* (2019.02); *G16H 10/60* (2018.01); *G16H 50/30* (2018.01)

(58) Field of Classification Search
CPC ........ G16B 20/00; G16B 40/00; G16B 50/00; G16B 99/00; G06Q 50/184; G06Q 10/10; G06Q 20/14; G06Q 20/40145; G16H 10/60; G16H 50/70; G16H 10/40; G16H 50/20; G16H 15/00; G06F 19/00; G06F 19/26; G06F 19/18; G06F 19/28
See application file for complete search history.

(56) References Cited

U.S. PATENT DOCUMENTS

| | | | | |
|---|---|---|---|---|
| 2008/0091464 | A1* | 4/2008 | Lipscher | G06Q 50/22 705/2 |
| 2013/0226621 | A1* | 8/2013 | Van Der Zaag | G06Q 50/22 705/3 |

* cited by examiner

*Primary Examiner* — Maroun P Kanaan

(57) ABSTRACT

A method of genetic testing utilizing a system of servers, databases, computers, software applications, or any other computing module. The computing modules allow for creation of a genetic test script and the analysis of genetic information based on the genetic test script. The system can also account for the use of proprietary biomarkers.

15 Claims, 10 Drawing Sheets

YOUGENE Live Demo

Home About Team Contact Patent Laboratory Prescription YouGene Internal

Create Prescription

Enter Physician ID for Sequence  234321234 — 801
Enter Patient ID for Sequence  5433443215134543 — 802
Enter Biomarker ID for Scan  5 - BRCA — 803
Is this a new or tumor specific scan?  New patient Sequence — 804

FIG. 8

YOUGENE Live Demo

Home About Team Contact Patent Laboratory Prescription YouGene Internal

Create Prescription

Scan Results for BRCA

Risk Factor    1.75X with 95% Confidence Interval between 1.09X and 2.80X

| BRCA1 gene SNP | Mutation | Measured | Detected | Matching Criteria |
|---|---|---|---|---|
| rs1799950 | G | TT | FALSE | Either Position in SNP Pair |
| rs4986850 | A | CC | FALSE | Either Position in SNP Pair |
| rs2227945 | G | TT | FALSE | Either Position in SNP Pair |
| rs16942 | G | CG | TRUE | Either Position in SNP Pair |
| rs1799966 | G | TT | FALSE | Either Position in SNP Pair |

1101        1102

| BRCA2 gene SNP | | | | |
|---|---|---|---|---|
| rs766173 | G | GA | TRUE | Either Position in SNP Pair |
| rs144848 | G | AG  1103— | TRUE | Either Position in SNP Pair |
| rs4987117 | T | CC | FALSE | Either Position in SNP Pair |
| rs2799954 | T | CC | FALSE | Either Position in SNP Pair |
| rs11571746 | C | TT | FALSE | Either Position in SNP Pair |
| rs11571747 | C | AA | FALSE | Either Position in SNP Pair |
| rs4987047 | T | AA | FALSE | Either Position in SNP Pair |
| rs11571833 | T | AA | FALSE | Either Position in SNP Pair |
| rs1801426 | G | AA | FALSE | Either Position in SNP Pair |

| ATM gene SNP | | | | |
|---|---|---|---|---|
| rs3218707 | C | GG | FALSE | Either Position in SNP Pair |
| rs4987945 | G | NO FOUND | FALSE | Either Position in SNP Pair |
| rs4986761 | C | TT | FALSE | Either Position in SNP Pair |
| rs3218695 | A | CC | FALSE | Either Position in SNP Pair |
| rs1800056 | C | TT | FALSE | Either Position in SNP Pair |
| rs1800057 | G | -- | FALSE | Either Position in SNP Pair |
| rs3092856 | T | CC | FALSE | Either Position in SNP Pair |
| rs1800058 | T | CC | FALSE | Either Position in SNP Pair |
| rs1801673 | T | AA | FALSE | Either Position in SNP Pair |

| CHEK2 gene SNP | | | | |
|---|---|---|---|---|
| rs17879961 | C | AA | FALSE | Either Position in SNP Pair |

| TP53 | | | | |
|---|---|---|---|---|
| rs1042522 | G | CC | FALSE | Either Position in SNP Pair |

FIG. 11

SYSTEMS AND METHODS FOR STORING, PROCESSING AND UTILIZING PROPRIETARY GENETIC INFORMATION

CROSS REFERENCE

The present invention is a continuation of U.S. patent application Ser. No. 14/483,921, filed Sep. 11, 2014, which is a continuation-in-part of U.S. patent application Ser. No. 13/371,422, filed Feb. 11, 2012, and U.S. patent application Ser. No. 14/452,979, filed Aug. 6, 2014, the entire contents of which are incorporated herein by reference.

FIELD OF THE INVENTION

This disclosure relates to methods and systems for conducting genetic testing, facilitating the use of proprietary biomarkers across users and facilitating payment for the use of intellectual property rights between users of the systems and methods.

BACKGROUND

The proliferation of studies employing genetic information has led to the increasing use of genetic information for diagnostic purposes. Physicians often gather information from a patient to access risk for various conditions such that further diagnostic tests, follow-up visits and prophylactic measures can be employed in an efficient manner. For example, a physician utilizing their professional judgment may decide that a patient having a family history of breast cancer warrants more frequent mammogram screening. Similarly, a patient having certain combinations of physiological and demographic parameters, such as sex, age, weight and height, and blood test results, may require preventive measures to forestall the development of heart disease, diabetes or other lifestyle diseases.

Recent advances allow for genetic profiles of individual patients to be developed without prohibitive costs. In addition to genetic information, metabolic, proteomic, and lipidomic data are increasing available for profiling individual patients in a clinical setting. Genetic, metabolic, proteomic, lipidomic and metabolic data can serve as biomarkers amenable to profiling risk for various diseases or conditions. For example, mutations in the BRAC1 and BRAC2 genes are used in clinical settings as biomarkers for indication of risk for developing breast and ovarian cancer. Alternatively, an analysis of the pI and quantity of specific proteins can indicate an on-going disease process before other symptoms are readily apparent.

Because the protein or enzyme levels of a patient can change over time, repeated tests using enzyme or protein analysis requires repeated samplings of the patient's blood. A patient's genome, however, is static and does not change with time. Once sequenced, the patient's genome can be used for multiple tests and can be used repeatedly into the future each time a biomarker test is needed. There is a need for a system that can scan a patient's genome and provide a diagnosis equivalent to known enzyme or protein tests.

Further, diagnostic tests employing the use of biomarkers are frequently protected by intellectual property rights usually in the form of issued patent claims. Often times, identifying the presence of particular biomarkers does not necessarily require the acquisition of materials or equipment from the owner of the intellectual property associated with the biomarkers. By means of example, the presence or absence of specific genomic mutations can be performed through the use of multipurpose sequencing equipment or genechips. Further, the number of laboratories and clinical settings having access to equipment for determining genetic information and other biomarkers is becoming increasing widespread as cost barriers are decreased. As such, the benefit of diagnostic intellectual property rights can be accessed through the use of increasingly standardized equipment without the need for acquiring any materials from the rights holder of the intellectual property in question.

Licensing for the use of intellectual property traditionally results from direct negotiation between the rights holder and one or more users or licensees. However, transaction costs become prohibitive when many potential users or licensees are present on the landscape. This is particularly true when potential users or licensees occasionally perform diagnostic tests associated with particular intellectual property rights. In addition, a diagnostic service may perform a test resulting in a wide range of information such as whole genome shotgun sequencing (WGS) or a genome-wide SNP analysis using a genechip, where a wide range of potential proprietary markers useful for diagnostic purposes can be revealed. However, the individual or organization performing the diagnostic service is unaware how the generated information may be used by other parties or what intellectual property rights may be implicated. A further complication is that certain diagnostic tests may require the evaluation of biomarkers that may be covered by multiple patents belonging to multiple different rights holders. The acquisition of a comprehensive profile of biomarkers associated with a specific condition may implicate patents owned by several different entities thereby creating large transactional costs in directly licensing the relevant intellectual property.

The need to negotiate and manage a large number of licensing agreements is a disincentive for potential users or licensees to respect the intellectual property rights of patent rights holders. Alternatively, the need to manage a large number of licensing agreements can discourage the use, development and/or validation of biomarker-based diagnostic techniques, particularly in situations where it is difficult to determine all the rights holders that may be implicated. This challenge has been recognized as creating "patent thickets," where commercial activity or legal compliance in an area is discouraged by a "thicket" of patent rights controlled by several different entities.

SUMMARY OF THE INVENTION

Disclosed herein are systems and methods for encoding and running biomarker tests and for facilitating licensing of intellectual property rights and transfer of payments between intellectual property rights holders (i.e. rights holders) and users or licensees. More particularly, systems and methods are disclosed for creating an algorithm for searching a patient's genome for particular biomarkers and reporting the results of the genetic test. The system and methods disclosed can also facilitate the use of proprietary biomarkers and genetic information by individual patients and transfer payments to interested rights holders when individual patients access or benefit from proprietary genetic information while ensuring patient privacy.

A method is provided for conducting a genetic test. A biomarker script is created that instructs the system on what portions of a genome the system should scan for particular mutations. The mutations of interest are defined and the system can determine the number of mutations corresponding to a biomarker that are present. Based on the mutations present, the system can determine a risk factor for a particular disease associated with the biomarker.

The method also facilitates transferring a payment to a rights holder of intellectual property rights in proprietary diagnostic information using a privacy facilitating system. Information contained in a patient records database is restricted such that one or more fields of information are not available to one or more users of the privacy facilitating system. The patient records database containing patient records including patient identification information and diagnostic information is accessed along with a proprietary records database containing records of proprietary biomarkers and rights holders of the proprietary biomarkers. Following accessing the databases, the patient records database and the proprietary records database are queried to determine the presence of a proprietary biomarker in a patient record of the patient records database and generating a result set including at least one results record. Optionally, the patient records database is updated to include the identification of a proprietary biomarker from the results record. Information obtained from the query is automatically forwarded or provided to one or more of a payer party user and a rights holder user associated with the proprietary biomarker used by the query of the patient records database. A payment or escrow between a payer party user and a rights holder user of the proprietary biomarker used by the query is accounted for by the privacy facilitating system.

A genetic testing system is provided. The system has a biomarker script database containing information corresponding to genetic mutations associated with a particular biomarker. The system can obtain a patient's genetic sequence and scan the sequence using the biomarker script in order to determine which, if any, mutations associated with the biomarker are present. The system can also provide a risk factor based on the number or identity of mutations found in the genome.

The genetic testing system can also have a privacy facilitating system or a payment system. The privacy facilitating system has a patient records database containing patient records including patient identification information and diagnostic information and a proprietary records database containing records of proprietary biomarkers and rights holders of the proprietary biomarkers. A patient information interface is configured to populate or update the patient records database, and a search engine facility is configured to query the patient records database and the proprietary records database to determine the presence of a proprietary biomarker in a patient record of the patient records database and generating a result set including at least one results record, where the results record contains patient identification information, payer party user information associated with the patient, and rights holder user information associated with the proprietary biomarker. A rights holders interface is provided and configured to allow selective access to the results record in accordance with privacy rules associated with the results record, and a payment facility is configured to account, process or escrow a payment from the payer party user to the rights holder user, with the proviso that the privacy facilitating system does not allow for the disclosure of patient identification information to the rights holder user. The payment facilitating system can have a search engine facility configured to parse the diagnostic information contained in individual patient records for the attributes of a proprietary biomarker and generate a results record associated with a specific patient record, wherein selective access to the results record is controlled by privacy rules. A payment log or database is provided containing information regarding a rights holder user having an intellectual property right in a proprietary biomarker used by the search engine and any payments due or made to the rights holder user and balances associated with specific patient records. A payment facility is provided that is designed to process, account or escrow a payment between a payer party user and a rights holder user having intellectual property rights in the proprietary biomarker identified by the search engine facility, wherein the payment facility processes a payment in a manner such that the rights holder user is blind to the patient identification information in the patient record having the proprietary biomarker identified by the search engine facility.

BRIEF DESCRIPTION OF THE DRAWINGS

FIG. 8 shows a screenshot of an exemplary prescription creation interface.

FIG. 9 shows a screenshot of an exemplary interface while the patient's information is obtained and scanned.

FIG. 10 shows a screenshot of an exemplary result of the scan for a patient with none of the defined genetic mutations.

FIG. 11 shows an exemplary result provided for a scan of a patient with some of the defined genetic mutations.

DETAILED DESCRIPTION

Figure 1:
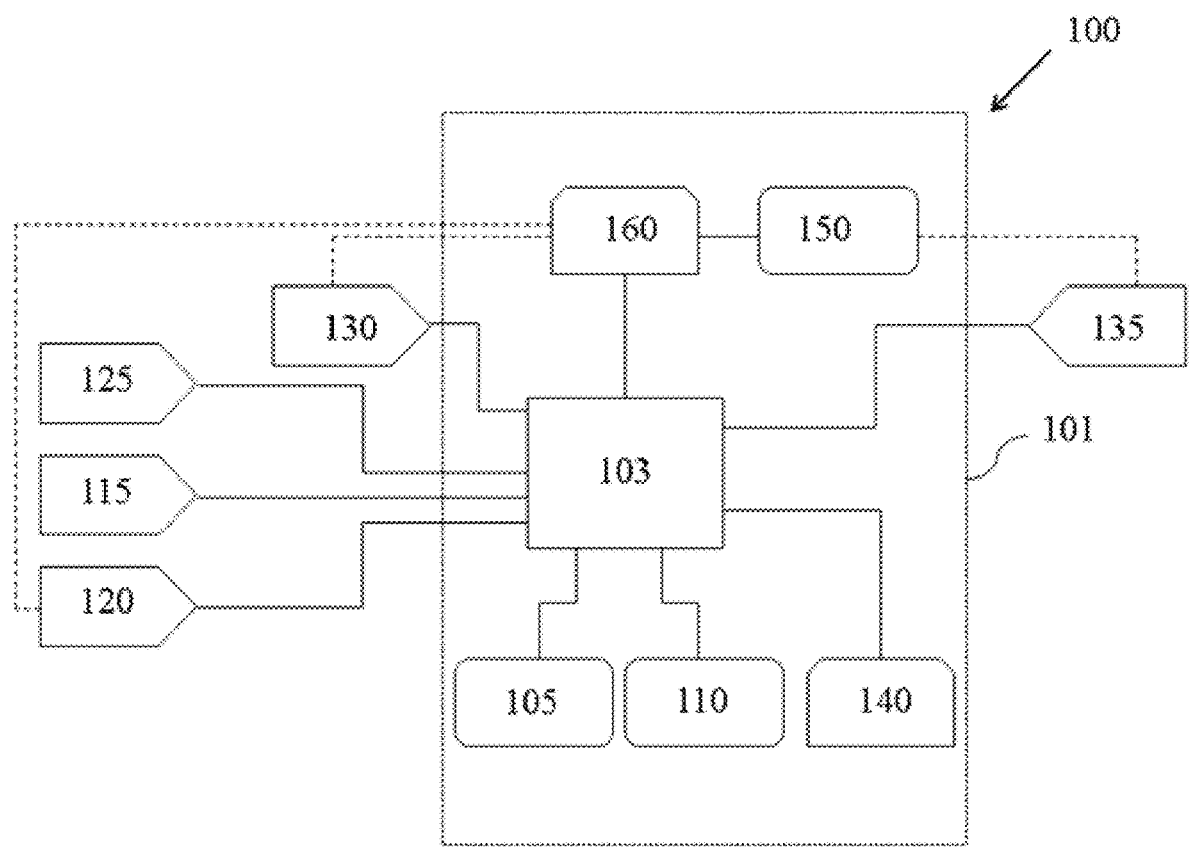
FIG. 1 shows a schematic for a system for facilitating the use of proprietary biomarkers across users and facilitating payment for the use of intellectual property rights between users of the system.

The systems of the invention are directed toward facilitating payment between a patient and/or the patient's insurance company (i.e. payer party) and rights holders of proprietary biomarkers including, but not limited to, proprietary genetic information. The system is designed to reduce time and cost barriers for providing payment to rights holders of proprietary biomarker information and thereby encourage legal compliance with intellectual property rights. Further, the system can be used as a tool to assist physicians in locating relevant biomarker information and making accurate diagnoses or assessments of risk for various medical conditions. Rights holders who provide instructions to receive payment information from the system benefit by increasing revenue sources to recoup investments in developing proprietary biomarker information and by reducing the burden in negotiating individual party license agreements and policing against infringement. When proprietary biomarker information is used to make a diagnosis or indicate a risk for a medical condition in connection with a patient profile in the system, payment can be forwarded in an automated fashion to rights holders in the proprietary genetic information used. The payment can be forwarded in a blinded fashion where the rights holder cannot ascertain the source of the payment and/or other information potentially useful in identifying a patient. Alternatively, the system can account for the need for a payment to be made or provide an escrow service for transferring payments between users. That is, the identity of the patient, and optionally, an insurance company or payer party forwarding payment to a rights holder can be hidden from the rights holder receiving the payment to protect against the unnecessary disclosure of information including sensitive genetic information.

Definitions

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "administrator" or "administrator user" refers to one or more individuals or parties responsible for maintaining the soundness and usability of the systems and methods described herein.

The term "authority" refers to having the right to access certain information stored in a system or database.

The term "biomarker" refers to a substance that whose quantitative or qualitative characteristics are used to determine a biological state or the presence or risk for a disease or condition. Biomarkers expressly include genomic information as indicated by a sequence or presence of certain nucleotide bases in a DNA molecule. Other express and non-limiting examples of biomarkers include quantitative or qualitative information regarding single nucleotide polymorphisms (SNPs), whole genome sequencing, genetic mutations, genetic linkage disequilibrium, metabolite information, proteomic information and lipidomic information.

A "biomarker script" is a set of computer readable instructions that cause the system to scan the genetic sequence for the presence of one or more particular biomarkers.

The term "comprising" includes, but is not limited to, whatever follows the word "comprising." Thus, use of the term indicates that the listed elements are required or mandatory but that other elements are optional and may or may not be present.

The term "consisting of" includes and is limited to whatever follows the phrase "consisting of." Thus, the phrase indicates that the limited elements are required or mandatory and that no other elements may be present.

The phrase "consisting essentially of" includes any elements listed after the phrase and is limited to other elements that do not interfere with or contribute to the activity or action specified in the disclosure for the listed elements. Thus, the phrase indicates that the listed elements are required or mandatory but that other elements are optional and may or may not be present, depending upon whether or not they affect the activity or action of the listed elements.

The term "database" refers to any organization of data or information that can be queried.

The phrase "equivalent to a known diagnostic test" means that the biomarker script determines the presence of the same genetic mutations as in the known diagnostic test. In the case of PCR based tests, this means that the biomarker script scans the genome for the same mutations for which the PCR based test provides probes. In the case of an enzyme based test, this means that the biomarker script scans the genome for the genetic mutations that give rise to the enzyme levels determined in the known test.

The term "field" refers to a category of information entered into a database, where the field contains the same quality or type of data between records.

The term "record" refers to a set of data present in a database that is associated with the same object such as a patient or biomarker.

The term "risk factor" refers to the change in probability of a patient developing a disease based on a particular factor or factors. The risk factors can be expressed as a multiple, such as 1.2×, wherein the probability of a patient with the particular factor developing the disease is 1.2 times greater than the probability of a patient without the factor developing the disease.

The terms "diagnostic service provider, "diagnostic service user" and "diagnostic service provider user" refer to a party or organization that performs tests or other laboratory work to generate information concerning the presence of biomarkers in a patient.

The term "diagnostic information" or "raw diagnostic information" refers to information generated from a laboratory or other test that contains biomarker information, where information regarding a biomarker need not be tagged, highlighted or identified within the diagnostic information.

The term "physiological parameter," "physiological data" or "physiological information" refers to here to refer to measurements of physiological functions that are not necessarily limited to the quantitative or qualitative of chemical substances and biomarkers. Non-limiting examples include sex, age, height, weight, blood pressure, heart atrial or ventricle pressure, heart rate, pulse, blood chemistry, glomerular filtration rate (GFR), EKG data, PET data, MRI data, and other data indicating the homeostasis or condition of the body.

The term "demographic parameter," demographic data" or "demographic information" refers to information that can be used to predict or determine the health status or risk for a disease or condition for an individual that does not necessarily require the physical examination of the individual. Non-limiting examples include medical history of the individual or relatives of the individual, life-style habits such as diet, exercise, smoking alcohol consumption patterns or sexual activity, prior medical procedures or medical appliances such as a pacemaker or a stent, exposure to environmental health risks, etc.

The term "clinical parameter," "clinical data" or "clinical information" refers to either physiological parameters or demographic parameters.

The term "payment" refers to the creation of a record detailing the obligation of one user of the systems or methods described herein to pay another user of the systems or methods described here. The actual receipt of financial funds is not necessary to complete a "payment." Rather, the financial funds can be escrowed by an administrator or another party who receives funds from one user and holds them for benefit of another user. Alternatively, payment can be completed by updating a log, database, or sending a notification that payment is due from one party to another where the transfer of financial funds can occur at some later time. However, a "payment" can also occur by the transfer of financial funds from one user to another user.

The term "privacy rules" refers to a set of rules implemented to control the level of access or authority for information stored on a system or database.

The term "proprietary biomarker" refers to a biomarker associated with certain intellectual property rights, where such intellectual property rights can include patent claims providing for specific methods for using, detecting or deriving information from the biomarker as well as compositions of matter for detecting the biomarker.

The terms "restricting," "restricting information," and similar terms refer to limiting the access to information stored on the system described herein or accessible using the methods described herein to specific users.

The terms "rights holder" or "rights holder user" refers to a user or party that is the owner of intellectual property rights for which the systems and methods described herein are providing payment for the use of subject matter within the domain of those intellectual property rights by other users or parties. Intellectual property rights specifically include patent claims but can also include other recognized intellectual property rights.

The term "payer party" or "payer party user" refers to an insurer or other party that is responsible for at least a partial payment to another user of the system and methods described herein. The payer party in addition to an insurance company can include a patient receiving the benefit of a diagnostic service.

The term "patient" or "patient user" refers to an individual, human or animal, from whom diagnostic information concerning biomarkers is taken.

The term "physician" or "physician user" refers to an individual, regardless of any licenses issued by a governmental authority, which uses the systems or methods described herein to identify or access biomarkers for purposes of making a medical evaluation using the systems or methods described herein.

The term "user" refers to any party or agent of a party who sends or receives information from the systems described herein or by means of the methods described herein.

The term "table" refers to an organization of data in a database.

The term "foreign key" refers to a parameter that serves as a restraint on data that can be entered on a database table.

The term "proteomic" refers to information relating to any of the quantity, identity, primary structure (sequence of amino acid residues), pI (isoelectric point), or any other qualitative information related to proteins present in a biological sample.

The term "lipidomic" refers to information relating to any of the quantity, identity, chemical structure, oxidation state or any other qualitative information related to lipids present in a biological sample.

The term "patient identification information" refers to any data that contributes to the personal identity of an individual.

The term "relational database" refers to a database that can be queried to match data by common characteristics found within the dataset.

The term "diagnostic test" refers to any process performed on a biological sample that results in information, termed "diagnostic information," about the sample. The "diagnostic information" can include, but is not limited to, genomic, proteomic, and lipidomic information regarding the biological sample and standard blood tests for determining blood chemistry.

Privacy Facilitating System for Transferring Payment to a Rights Holder

The systems and methods disclosed herein provide for the linkage of patient- and/or specimen-centric molecular, genetic or other biomarker data to proprietary information useful for making medical diagnoses or risk assessments. The described systems can search multiple databases, indexes, catalogs or databases, and in various languages, for patented or proprietary genetic biomarkers and related information to populate and maintain the system database(s). Genetic biomarkers can include polymorphisms, linkage disequilibrium of alleles at multiple loci, and mutations in genomic or mitochondrial DNA. The systems can receive input from a third party database or databases where the third party database can automatically upload new proprietary genetic information. The system database(s) contains proprietary genetic information and/or biomarkers including owner information, clinical, diagnostic, and treatment data. The system database(s) can further contain error logs and/or audit logs to document data inconsistencies in the system database(s). Those skilled in the art will readily recognize that the data structure for maintaining the databases is not particularly limited and can, for example, employ a relational database management system or an object-oriented database management system.

The system also has a component for storing patient information in a system patient records database(s). A physician user or another user can enter the patient's clinical data including medical history, attributes, physiological parameters, demographic parameters and/or laboratory test results in appropriate fields of a database. The system patient database(s) also contains information for genetic biomarkers or other biomarkers associated with specific patients. In some cases, a patient's biomarker information, such as, for example, Single Nucleotide Polymorphism (SNP) information, will be unknown at the time of examination or diagnosis by a physician. Therefore, in certain embodiments, the physician or another user can enter the patient's biomarker information into the system patient database(s) at a later time. In light of the increase in personalized medicine, patients are increasingly encouraged to actively engage in the collection and management of their personal health records. As such, in certain embodiments described herein, a patient-centric model for determining usage of proprietary biomarker information is employed where the determination of the need for payment to stakeholders can be triggered on the patient level rather than as a result of a licensing agreements or other relationships between the rights holders in particular biomarkers and particular diagnostic labs or physicians.

In other embodiments, diagnostic laboratories or physicians can perform required tests to determine patient biomarkers and directly upload the information into the system patient records database(s). The system can then correlate the patient's clinical and/or biomarker information with information in the system database(s), and/or access one or more public or private domain databases and generates a match for any proprietary biomarker information. In addition, a patient's clinical and/or demographic information can be compared with other patient records in the patient records database(s) to determine whether common attributes are present in the population identified by the system as sharing a common SNP or other biomarker for use in diagnosis and treatment. Information can then be communicated to the physician indicating that the individual shares attributes with a population of individuals having a common SNP or other biomarker. Accordingly, this method provides a means for identifying patients possessing genetic information and biomarkers that might read on proprietary uses and methods of utilizing the information. Further, notice to insurance companies or payer parties and payments to stakeholders of proprietary information can be made in an automated fashion.

With reference to FIG. 1, systems for implementation of the innovations disclosed herein will be described. In FIG. 1, a system 100 having a trusted server 101 (inside dashed rectangle) is provided to control access to one or more databases and manage the transfer of payment between users. Those skilled in the art will understand that trusted server 101 may be any configuration of one or more processors 103 (rectangles), data storage devices (rounded rectangles) and servers for communication capable of performing the functions disclosed herein. The system 100 can host various user interfaces (pentagons) and functional facilities (hexagons). The trusted server 101, and more particularly the one or more processors 103, controls access to information stored in a proprietary records database 110 and a patient records database 105 according to privacy rules that govern access to information contained in the proprietary records database 110 and the patient records database 105.

The patient records database 105 contains individual patient records that include patient identification information and diagnostic information, where each patient record is associated with a particular individual patient. The individual patient identification information can include such fields as first and last name, data of birth, physician information, address, social security or other identification number, or any other information that may potentially give an indication as to the identity of the patient associated with the identification information. Those skilled in the art will appreciate that the patient records database 105 is not limited to any particular device or hardware.

The proprietary records database 110 contains records of proprietary biomarkers, information regarding the rights holders of the biomarkers, and data or rules for the use of the biomarkers to diagnose specific diseases or conditions or indicate risk for specific diseases or conditions. In addition to biomarkers, the proprietary records 110 database can optionally contain demographic or clinical information that can be used to evaluate risk for specific diseases or conditions. Many biomarkers have increased predictive power when used in combination with certain demographic and/or physiological parameters. For example, the presence of a specific SNP may indicate an increased risk for certain diseases or conditions in combination with certain demographic and/or physiological parameters or information, such as age, sex, weight, height, blood pressure, EKG characteristics or certain prior medical history such as a vascular stent. Alternatively, the presence of specific SNP may indicate a particular therapeutic regimen such as administration of drug or use of a medical device. In particular, the presence of a SNP may indicate the implantation of an Implantable Cardio defibrillator Device (ICD). In some instances, the patent claims of a rights holder may only extend to the use of one or more biomarkers in combination with certain demographic and/or physiological parameters. In such instances, the intellectual property rights of a rights holder may only be implicated when a biomarker is present in a patient record in conjunction with certain demographic and/or physiological parameters.

A function of the system 100 is that access to the information in the patient records database 105 is restricted. Regarding information in the proprietary records database 110, the extent and owners of intellectual property rights, particularly patent rights, is usually publically known. As such, access to information in the proprietary records database 110 does not need to be restricted in certain embodiments. In particular, access to patient identification information is restricted to protect the privacy of the patients. In some embodiments, access to patient identification information is only granted by the privacy rules to a patient's physician and optionally a payer party having responsibility for a patient. Access to demographic and clinical information and biomarkers can be granted for the purposes of making comparisons between populations, as described above.

Medical information is oftentimes regarding as personal by many individuals, where disclosure of medical information that can be associated with a specific individual is often times regarded as a violation of trust or an intrusion into personal privacy under social norms. In addition to the social sensitivity of medical information, physicians and other medical providers can have ethical or legal obligations to shield the privacy of patient medical information. Still further, the presence of certain biomarkers, particularly genetic information, can be used to discriminate against specific patients. For example, knowledge of particular genetic information may be used by employers to discriminate in hiring or by health insurers to decline coverage. The potential illegality of such discrimination is not an absolute deterrent to its occurrence.

Medical information is entered into individual records in the patient records database 105 via a physician user interface 115 or a diagnostic service provider interface 120. As shown in FIG. 1, the physician user interface 115 is in communication with the trusted server 101. The physician user interface 115, in certain embodiments, is located on an internet web server where the physician user interface 115 can be accessed using a standard HTML web browsers. In other instances, the physician user interface 115 can be a specialized executable program running on a processor remote from the trusted server 101 or processor 103, where communication with the trusted server 101 is accomplished through the internet or other network.

The physician user interface 115 is accessible by a user having authentication credentials to identify the user as a physician user 115. A physician user 115 is a health care provider or an individual supervised by the health care provider who is authorized by a patient to enter or populate information associated with a specific patient record in the patient records database 105. A physician user 115 can have the ability to enter information into a patient record including patient identification information and demographic information either manually or in an automated fashion through electronic data provided by a separate electronic records system maintained by the physician user. Security rules can be set such that the physician user has access to the information contained in a patient record for which the physician has authority but not to identification information for patient records for which the physician does not have authority.

The authority of a physician user for a particular patient record in the patient records database can be established automatically upon the establishment of a new patient record. That is, the possession of identifying patient information used to establish the patient records presumes that the physician user has authority concerning that patient. Alternatively, the authority of a physician user can be verified or certified by a physician user already having access to the system, for example, where a patient switches medical providers. Alternatively, a patient user interface 125 can optionally be provided to allow the patient to designate the authority of a specific physician user. In certain embodiments, the patient user interface 125 does not have access to change the content of the patient records in the patient records database 105 to prevent an unsophisticated user from inadvertently changing the content of the patient record.

Optionally, the trusted server 101 can also be accessed through a diagnostic service provider interface user 120. Biomarkers are physical traits that are determined through laboratory testing often requiring sophisticated equipment. As such, a specialized testing laboratory or diagnostic service may be employed to directly perform diagnostic tests and generate diagnostic information. The diagnostic information can be reported to the physician whereupon the physician may update the diagnostic information contained in a patient record through the physician user interface 115. Alternatively, the diagnostic service provider user interface 120 may be provided to allow the testing laboratory or diagnostic service to directly update the diagnostic information of a patient record in the patient records database 105. The diagnostic service user interface may be accessible through an HTML viewer or a specialized executable program in a manner similar to the physician user interface 115.

The privacy rules operating on the trusted server 101 can be configured to allow a physician user a large degree of access to the patient records of the patient records database 105 for which the physician has authority, since a physician generally requires access to all of the patient identification information and diagnostic information contained in a patient record. In contrast, a diagnostic service provider typically does not need to have any significant access to patient information. As such, the privacy rules can be set to allow the diagnostic service provider to use the diagnostic service provider user interface 120 to upload diagnostic information to the patient records database 105. In certain embodiments, the diagnostic service provider need not be informed or have access to basic patient identification information such as name and date of birth. Rather, unique and/or one-time reference number for the particular diagnostic test can be provided to the diagnostic service provider while the trusted server 101 can correlate the reference number with a particular patient record to be updated.

Additional users of the system include a payer party user and a rights holder user, who access the trusted server 101 through a payer party interface 130 and rights holder interface 135, respectively. A function of the system 100 is to allow for the transfer of payment from a payer party to a rights holder when proprietary biomarker information is accessed through the physician user interface 115. The process for a physician to access proprietary biomarker information using the system 100 will be described in greater detail below.

Health care services, including diagnostic tests for biomarkers and physician treatment and advice based upon the presence of biomarkers, are often covered by health insurance where the patient receiving the services is not responsible for 100% of the necessary payment. The payer party user in some embodiments is a health insurer or other third party payer having responsibility for a specific patient represented by a patient record in the patient records database 105. Further, the patient themselves may also be responsible for all or part of the payment due for accessing certain proprietary biomarkers in the course of their care by a physician. As such, the payer party can further include a patient in addition to or in place of an insurer.

The privacy rules operating on the trusted server 101 can be configured to allow the payer party user access to only information necessary to verify the obligation to authorize a payment or review the validity of payments already sent. In some embodiments, the payer party user need not have access to the nature of the diagnostic query or test actually performed, rather only a guarantee that the service performed is of the type normally authorized by a specific health plan. As such, a patient record in the patient records database 105 can contain details of the identity of a payer party for that patient along with details of the extent of medical coverage provided by the payer party. A payer party user can choose to receive notification, as set in the privacy rules, that an insured patient has received an evaluation based upon proprietary biomarkers covered by insurance and choose to allow payments to processed without knowing the precise identity of the biomarkers concerned, although the payer party user can require the identity of the insured patient to verify coverage. As such, the system 100 can guarantee a high degree of patient privacy for sensitive medical information.

Typically, payer parties and insurers have access to the nature of medical diagnostic tests performed on insured persons, where such medical diagnostic tests are billed to the insurer. Here, a diagnostic service provider can still directly bill a payer party or insurer directly for their services performed as is the usual custom. For example, a diagnostic service provider can bill a payer party or insurer for the performance of a genome-wide SNP analysis using a genechip or similar test or a blood protein analysis; the nature of these diagnostic tests may be directly reportable to the payer party or insurer. However, as will be explained below in greater detail, the system 100 allows a physician user to access information concerning specific biomarkers measured by such tests. While a payer party user or insurer may have knowledge that a genome wide SNP analysis was performed on a specific insured patient, the payer party user's access to knowledge that a physician specifically evaluated biomarkers related to heart disease, cancer or other specific diseases or conditions can be shielded using the privacy rules of the system. Alternatively, payments to and from a diagnostic service provider user can be made through the system 100 as necessary to protect confidential patient information.

Similarly, a rights holder user typically does not require access to the identity of a patient or physician that has accessed information related to specific proprietary biomarkers. As such, the privacy rules can be configured to allow the rights holder user interface 135 to access information regarding the frequency of use of their proprietary biomarkers and verify the receipt of proper payment. However, the identification information of patients as well as the names of physicians and insurers can be shielded by the system 100 as required.

Those skilled in the art will readily understand that the privacy rules described above can be modified from the description above as required by certain users. For example, a payer party user can require a greater degree of information to authorize or review payments for the use of certain proprietary biomarkers, and the privacy rules can be modified to vary the degree of access to identification information and diagnostic information contained in the patient records database 105. The system 100 facilitates anonymous transfer of rights to use proprietary biomarkers and the anonymous transfer of payments to rights holders in such proprietary biomarkers. The invention specifically contemplates the use of any set of privacy rules that fulfill the aforementioned criteria.

The system 100 can include an optional notification server 140 that functions to send an email or other notification to any user containing the availability of new information from the system or a notice that new information is available upon accessing the appropriate interface. Such notification can be done using email or like notification or displayed by prompt upon a user logging into the system 100 after new information becomes available.

Figure 2:
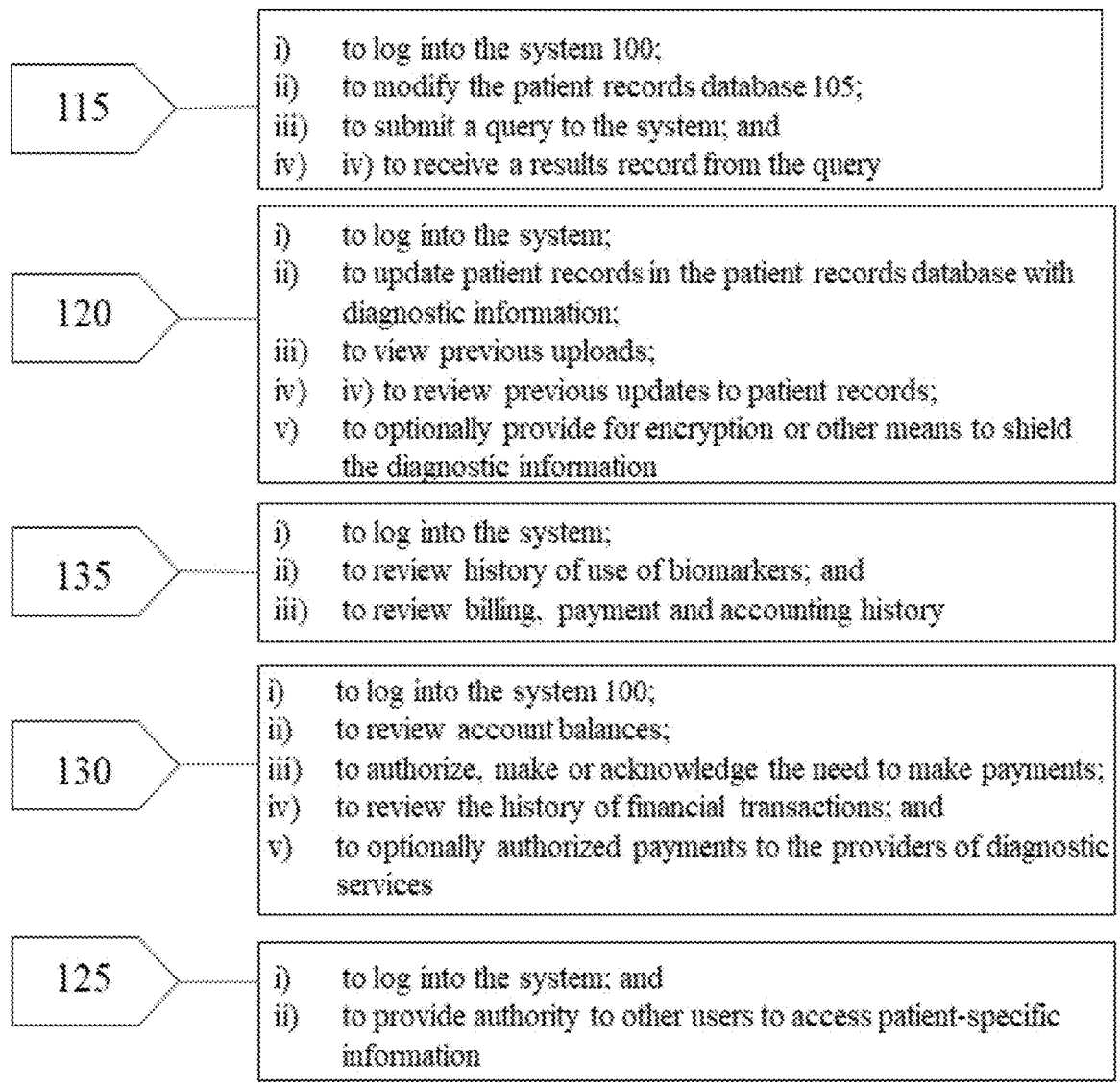
FIG. 2 shows the functionality of user interfaces of the system.

With reference to FIG. 2, the access to the patient records database 105 and privileges granted to different categories of users will be discussed. The physician user interface 115 provides the ability i) to log into the system 100; ii) to modify the patient records database 105 for authorized patient records including patient identification information and diagnostic information; iii) to submit a query to the system 100; and iv) to receive a results record from the query by email or by logging into the system 100. The diagnostic service provider interface 120 provides the ability i) to log into the system; ii) to update patient records in the patient records database 105 through use of a reference ID number and/or a doctor ID number with diagnostic information; iii) to view previous uploads; iv) to review previous updates to patient records and v) to optionally provide for encryption or other means to hide the diagnostic information from a technician performing the transfer of data to the system 100.

The rights holder user interface 135 provides the ability i) to log into the system; ii) to review history of use or matches of proprietary biomarkers associated with the rights holder user; and iii) to review billing, payment and accounting history for use or matches of proprietary biomarkers. The payer party user interface 130 provides the ability i) to log into the system 100; ii) to review account balances for insured patients; iii) to authorize, make or acknowledge the need to make payments to rights holder users; iv) to review the history of financial transactions; and v) to optionally authorized payments to the providers of diagnostic services. The patient user interface 125 provides the ability i) to log into the system; and ii) to provide authority to other users to access patient-specific information.

Querying the System

As describe with regards to FIG. 1, the system 100 contains a trusted server 101 that functions to interact with users and implement privacy rules to control access to the patient records database 105. The physician user interface 115 and optionally the diagnostic service interface 120 are used to populate the patient records of the patient records database 105 with diagnostic information. The diagnostic information can contain a large quantity of data that requires analysis to determine the presence of proprietary biomarker information. For example, the diagnostic information can contain genome-wide genetic information that requires parsing to identify the presence of certain alleles, SNPs or mutations.

In certain embodiments, the diagnostic information is only accessed in regards to a specific query from a physician initiated through the physician user interface 115. As such, only biomarker information that is used by a physician to assess the risk for a specific disease or condition of concern is granted to the physician user, where such access results in the potential need for payment to a rights holder. For example, if genome-wide information is taken for a patient and present in the diagnostic information in the patient record, many potential proprietary SNPs or other biomarkers can potentially be present in the acquired diagnostic information. However, it would be impractical under most scenarios to require payment for all the proprietary SNPs that may be present in an individual patient's genome as determined through genome-wide diagnostic information. Further, the intellectual property of rights holders may only extend to certain uses of particular proprietary SNPs rather than only detection during a diagnostic test. Further, intellectual property rights may only extend to multiple biomarkers and/or clinical parameters present in one patient for the indication of risk for a specific disease or condition.

As such, a physician user can access the diagnostic information in a patient record by querying the system 100 with at least one search criterion. The search criterion can be specific biomarkers and/or a search for biomarkers that are correlated with specific diseases or conditions. Search algorithms and methods to parse through genetic information are known. Other biomarker data, such as lipidomic and proteomic data, can also be searched in response to a query.

The proprietary records database 110, in addition the identity of specific biomarkers, can contain information regarding specific diseases or conditions associated with certain biomarkers. Often, these specific diseases or conditions are specified in the patent or other intellectual property grant upon which the associated rights holder relies upon. Specific diseases or conditions can be assigned unique codes for use within the system 100 to avoid the uncertainty of key word searching.

By means of a non-limiting example, a physician can request a whole or partial genome evaluation of a patient, where the generated diagnostic information is loaded into the patient record in the patient records database 105. The physician can then submit a query to the system 100 through the physician user interface 115 to search for SNPs associated with the risk for heart disease. In certain embodiments, the trusted server 101 or another processor can iteratively search the genetic information contained in the diagnostic information for proprietary biomarker SNPs and/or other SNPs associated with heart disease. Known search engines and parser algorithms such as BLAST, BioJava (http://www.biojava.org/wiki/Main Page) or BioParser (http://bio-informatics.tgen.org/brunit/software/bioparser/) can be used to search the diagnostic information for relevant proprietary biomarkers. A sub-database table or results record can be populated in the relevant patient record of the patient records database 105 with the information extracted using the parser algorithm, which will eliminate the need to parse the raw diagnostic data only one time to extract biomarkers relevant to the query.

Upon the identification of proprietary biomarkers in response to a physician query, the intellectual property of one or more rights holders can be thereby used and the process to transfer, to account for or to escrow a payment to the rights holders can then be initiated. The trusted server 101 updates a payment log or database 150 to credit an appropriate rights holder user with a monetary amount for use of proprietary biomarkers upon a successful query by a physician user that returns proprietary biomarkers in response to the query. A payment facility 160 can be present to process payments from a payer party user to a rights holder user. Payment can be automatic or only after authorization by a payer party user using the payer party user interface 130. In certain embodiments, the system 100 does not complete an actual transfer of funds between bank accounts. Rather, payment is completed for the purposes of the invention and the attached Claims when a balance in a payment log or database 150 is updated reflecting the obligation of a payer party user to remit funds. Funds can be remitted by payer parties to an Administrator of the system 100 or another party in escrow on a periodic basis, at which time the Administrator can send funds to the appropriate rights holders, and the remittance of the payment noted in the log or database 150. In other embodiments, the payment facility 160 can be programmed with the banking information of the relevant users and periodically initiate payment between the payer party users and the rights holder users using the automated clearing house (ACH) or other electronic means in a manner that ensures the anonymity of the rights holder user and the payer party user. Funds may be first transferred through a bank account set-up for the administration of the system to protect the identity of the payer party, which may in turn reveal patient identification information.

If one or more rights holder users own rights to the returned proprietary biomarker information from the query in the results record, an agreed upon calculation can be used to divide payment from a payer party user automatically between the rights holders of the proprietary biomarker information using the system 100. For example, a first rights holder user can own patent claims for a first SNP biomarker to indicate heart disease risk, and a second rights holder user can own patent claims for a second SNP biomarker to indicate heart disease risk. The system 100 and the payment facility 160 can automatically and simultaneously inform both the first and second rights holder users of the found biomarkers in one patient, and then a pre-arranged calculation can be performed to apportion payments to each rights holder user. In this manner, individual patient costs can be distributed across all patients using the system 100 whereby using the systems and methods of the invention, the rights holder users are blinded to specific patient identification information.

An additional feature of the system 100 is that the use of proprietary biomarkers can be attributed to a specific patient. That is, the patient record can be annotated to indicate, for example by means of the results record, that the use of particular biomarkers have been accessed and paid for in the past. In certain embodiments, a patient can go to another physician to get a second opinion and/or the same or a different diagnostic test can be performed that implicates biomarkers for which payment has already been made in the past. The patient can be granted a limited license to allow for the future use of a proprietary biomarker accessed in the past. As such, the patient can get a second physician's opinion and/or an additional diagnostic test without additional payment.

For example, a patient record can be updated to indicate proprietary biomarkers that have been accessed in the past and payment previously made. If a future query is made that generates a results record containing a previously accessed biomarker, the system can be set to allow further usage of that proprietary biomarker without additional payment. In certain embodiments, the length of time for which future use can be made of a previously accessed proprietary biomarker can be limited to a set period of time. The patient record can be annotated to indicate a date that a biomarker was first accessed to allow the calculation of the expiration a license for future use, where the amount of time rights to use of a biomarker can be indicated in the proprietary records database 110.

The system can also correlate a patient's demographic and physiological information with information in the system and/or accessed from one or more public or private domain databases, such as a SNP consortium, and generating a result set that includes a suggestion for genetic, proteomic, and/or other type of diagnostic testing. In a further embodiment, the present invention also relates to displaying the identified correlation to aid in determining the statistical significance of the identified correlation. In addition, the patient's diagnostic, clinical and physiological information may be compared with other patient records in the database to determine whether common attributes are present in the population identified by the system of the invention as sharing common biomarkers for use in diagnosis and treatment. Information can then be communicated to the physician indicating that the individual shares attributes with a population of individuals having a common biomarker. Such information can be included with the results record generated the physician's query.

Figure 3:
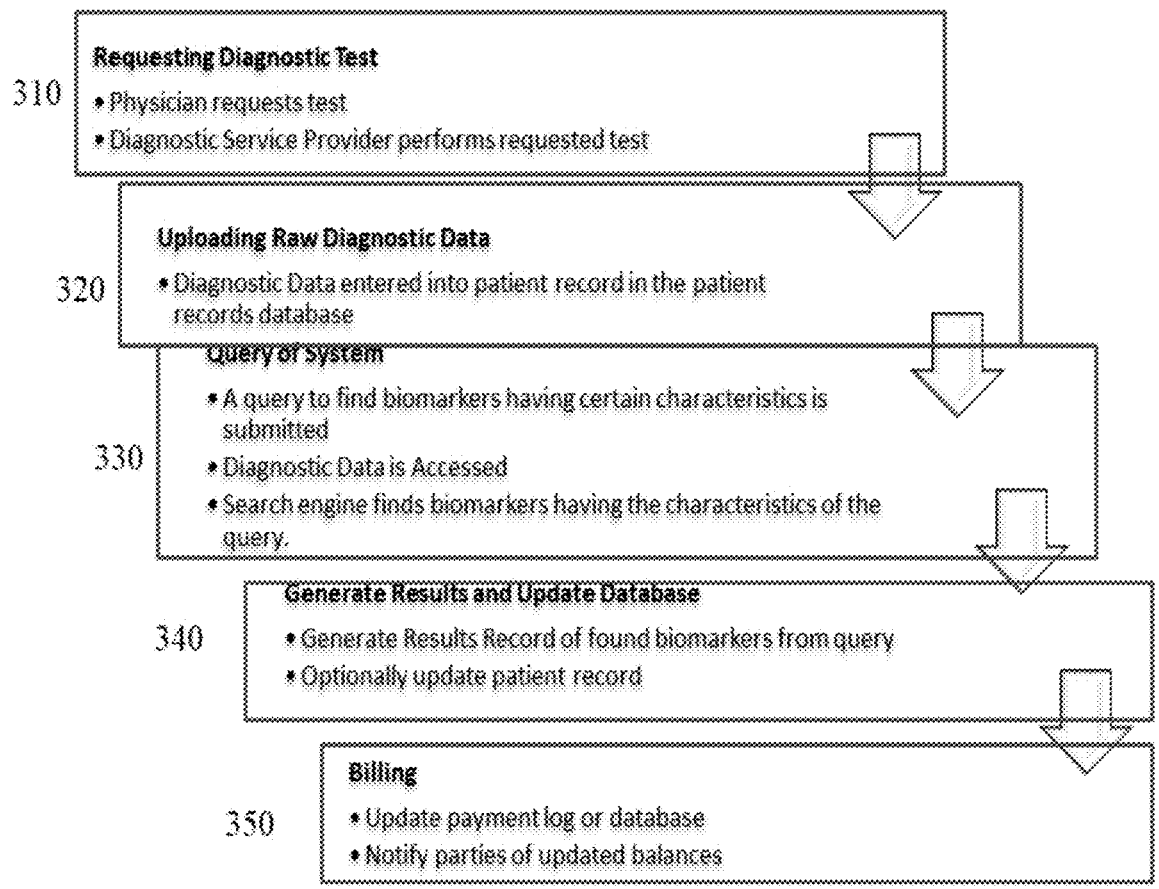
FIG. 3 shows a flow chart for querying the system for the presence of proprietary biomarkers in a patient record.

With reference to FIG. 3, an exemplary process to query the system 100 for proprietary biomarkers and remit payment to a rights holder user in a blinded fashion will be described. In step 310, a physician requests a certain diagnostic test be performed, where the raw diagnostic data generated by the diagnostic test can include proprietary biomarkers. In step 320, the raw diagnostic data is uploaded to the system 100 for addition to a specific patient record in the patient records database 105. The raw diagnostic data can be uploaded by a diagnostic service provider and the patient record identified by a reference number that maintains the anonymity of the patient. In other embodiments Step 320 can occur prior to Step 310 and the data previously uploaded can be recalled from the system 100.

In step 330, a physician prescribes system 100 query the raw diagnostic data to look for attributes of the biomarkers in the raw diagnostic data and/or to look for biomarkers predictive or indicative for risk for specific diseases or conditions. The patient's record database is accessed by the system 100 and the raw diagnostic data is parsed to identify proprietary biomarkers having characteristics conforming to the query. In step 340, a results record is generated containing biomarkers returned by the query and optionally the physician and/or a payer party user having responsibility for the patient or rights holder user associated with the propriety biomarkers are notified. The patient record can be updated with the contents of the results record or the query. In step 350, a payment log or database is updated to reflect the need for a payment between a payer party user and a rights holder user in a blinded fashion.

Database Structure

Figure 4:
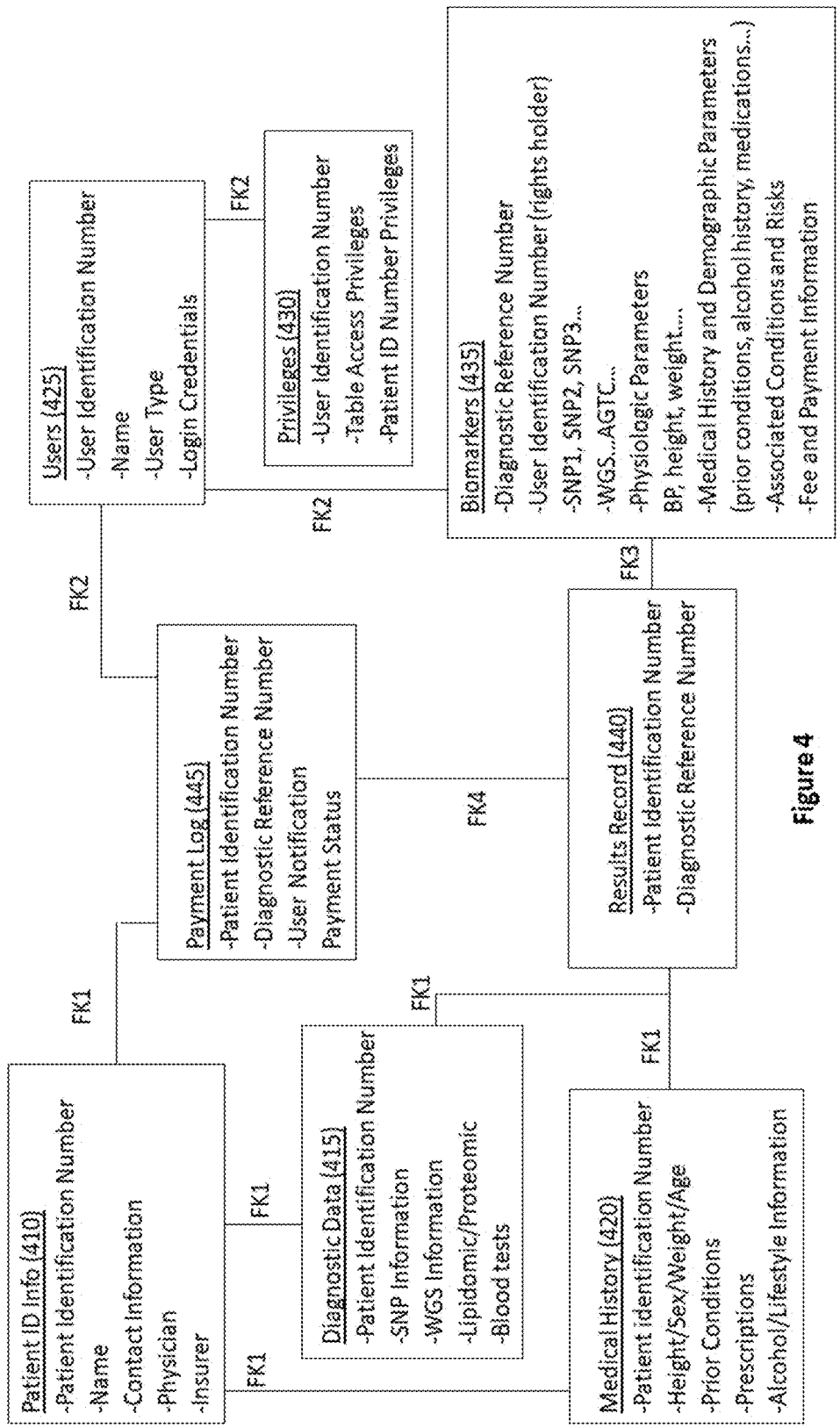
FIG. 4 shows an exemplary relational database structure for a system for facilitating the use of proprietary biomarkers across users and facilitating payment for the use of intellectual property rights between users of the system.

FIG. 4 shows a non-limiting example of a database structure that can be employed in conjunction with the methods and systems described herein. Those skilled in the art will readily recognize that other database structures and organizations can be equally employed to practice the methods and systems described here. FIG. 4 illustrates a structure for a relational database that can be accessed and search queries obtained through the use of structured query language (SQL).

FIG. 4 shows a relational database having several Tables having rows and columns related to the category stated in the header. As presented in tables 410-445 in FIG. 4, exemplary attributes for each table are listed. The first attribute in each of tables 410-445 can be used as a key to relate information in that table to another related table using SQL. More specifically, the first attribute in each table can serve as a candidate key that is not duplicated within any one table. The organization of tables 410-445 will now be described.

Table 410 contains patient identification information. The attributes can include a patient identification number, the patient's name, contact information, physician name and/or physician user identification number, and insurer information and/or payer user identification number. Those skilled in the art will readily recognized that other attributes may be contained in patient identification table 410. As described, protection of the information contained in the patient identification information table 410 is strictly controlled in order to protect patient privacy. As such, sensitive information regarding patient identity can be segregated on table 410 to prevent unauthorized disclosure of such information.

Data and information associated with specific patients that may have less strict control over access can be stored on tables separate from table 410. As shown in FIG. 4, a diagnostic data table 415 can be provided. In addition to containing the patient identification number attribute, table 415 can contain additional attributes related to various diagnostic tests performed on the patient associated with a patient identification number. Examples of attributes that can be provided on the diagnostic data table 415 include the presence of specific SNPs, WGS, WES, or targeted gene information, proteomic and/or lipidomic information, and results of blood tests reflecting blood chemistry. Similarly, table 420 can contain information regarding a specific patient's medical history. In addition to containing the patient identification number attribute, table 420 can contain additional attributes such as previous diagnoses, current prescriptions, height, weight, age, and other attributes typically contained in medical records. Specific attributes of tables 415 and 420 may be represented by a reference numeral rather than a word string to facilitate querying of the system.

Tables 415 and 420 can be constrained through the use of a foreign key, shown as FK1 in FIG. 4. The foreign key FK1 can be used to insure that a patient identification number attribute on tables 415 and 420 occurs and has a valid entry on patient identification information table 410. The foreign key FK1 can also be used as a constraint to ensure that a patient identification number contained on other tables, as shown in FIG. 4, occurs on tables sharing a relationship. For example, the foreign FK1 can constrain the system or any user from entering information on diagnostic data table 415 with a patient identification number that does not appear as an attribute on patient identification information table 410.

As described, the systems described herein provide for various user interfaces for interacting with the system including entering information in the system and submitting a query. User table 425 can have attributes including user identification number, user name, user type, and login credentials. The user type (e.g. physician user, rights holder user, etc.) can be used by the system to present the appropriate user interface to a user logging onto the system. The user table 425 can be related to a privileges table 430 that defines the access rights within the privacy rules operating on the system including which patient identification numbers certain users have privileges and concerning access to patient identification table 410. Foreign key F2 can be implemented to constrain privilege table 430 to only contain user identification number attributes that appear in user table 425.

Biomarkers table 435 can be further related to user table 420. Biomarkers table 435 contains the combination of biomarkers and other information that represent the intellectual property owned by specific rights holder users. In general, the user identification number attributes on table 435 are associated with rights holder users. A diagnostic reference number can be provided as an attribute that represents discrete diagnostic tests that represent an intellectual property right held by a rights holder user.

For example, a certain combination of biomarkers can represent an increased risk for cancer. By means of illustration, a rights holder can be the holder of a patent claim that recites that the presences of a G nucleotide at SNP1, and a C nucleotide at SNP2, and a weight above 200 pounds for males represents an elevated risk for certain kinds of cancers, where SNP1 and SNP2 represent specific genomic loci in the genome. The biomarkers SNP1 and SNP2 and the clinical parameters regarding weight and sex can be organized in the same row of biomarkers table 435 associated with a unique diagnostic reference number attribute. FIG. 4 shows non-limiting examples of biomarkers including SNPs, WGS, proteomic and/or lipidomic information, physiological parameters, and demographic parameters that can be associated with specific intellectual property rights. The rows of table 435 can also contain fee information associated with the use of the diagnostic test represented by that row of the table 435.

As described above, the system can be queried to identify patients having specific biomarkers or combinations of biomarkers and/or clinical parameters that represent an elevated risk or decreased risk for certain diseases and conditions. The search engine associated with the system can search for the concurrence between the specific intellectual property rights stored in biomarkers table 435 with the information stored on the diagnostic data table 415 and the medical history table 420. As described, the system, for example, can be queried to determine if a specific patient has any biomarkers and/or clinical parameters associated with an increased risk for cancer. The system will then systematically search the appearance of any combination of biomarkers and/or clinical parameters associated with a diagnostic reference number annotated to be correlated with a risk for cancer against the information stored in diagnostic data table 415 and/or medical history table 420.

Any matches from a query can be recorded in results record table 440 as shown in FIG. 4. The results record table 440 can list the patient identification number for the patient having at least one match to a diagnostic reference number. A foreign key FK3 can be employed to constrain results record table 440 to contain only diagnostic reference numbers that appear on biomarkers table 435. A payment log table 445 can be provided to record activity of the payment facility 160. The payment log table 445 can contain the patient identification numbers and diagnostic reference numbers representing a match from a query as in results record table 440. A foreign key FK4 can be provided to constrain payment log table 445 to only contain entries for combinations of patient identification number attributes and diagnostic reference number attributes that occur in results records table 440. The payment log 445 can contain further attributes concerning the status of notification to users regarding payments and the status of any pending payments between any users of the system.

Hardware

Figure 5:
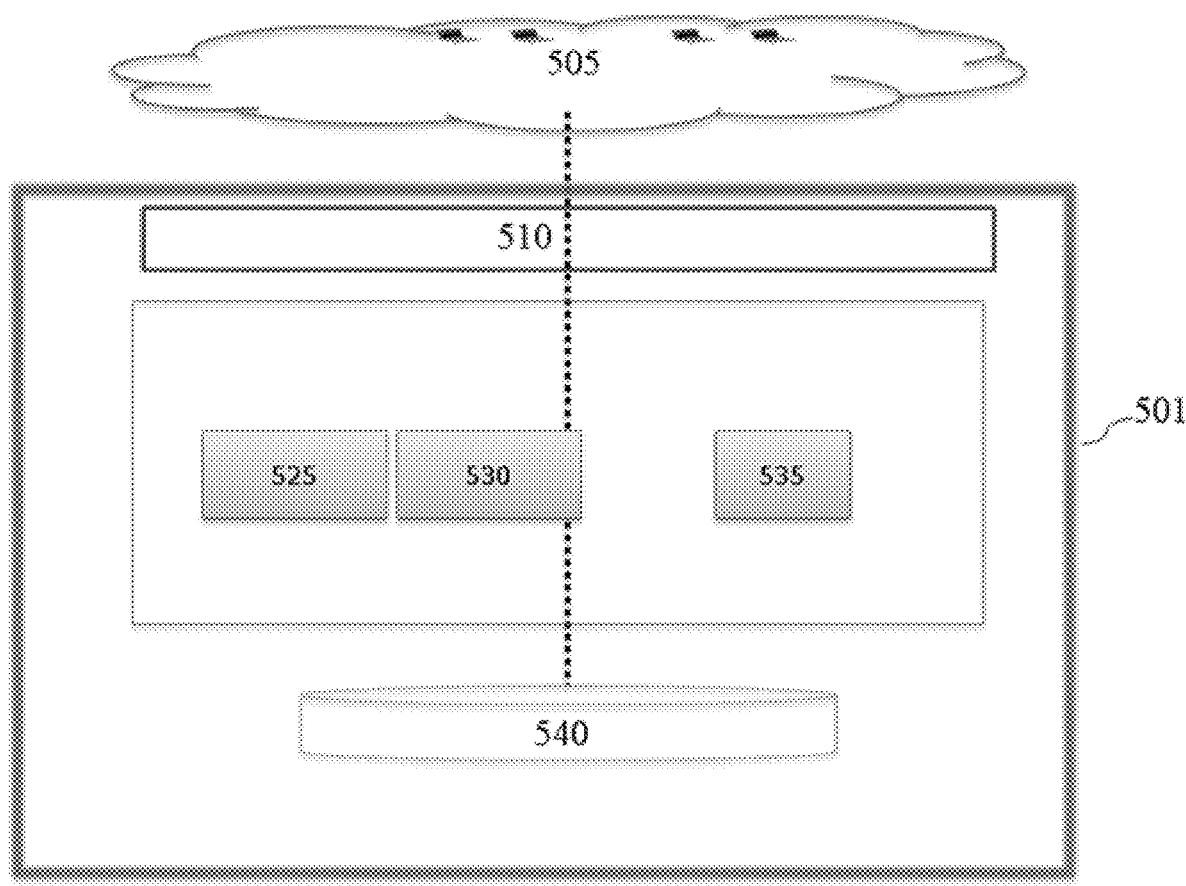
FIG. 5 shows an exemplary hardware implementation for implementing the methods described herein.

FIG. 1 illustrates the functionality of the systems and methods disclosed herein. The above-described functionality can be implemented on any hardware system adaptable to carrying out the above described functions. However, non-limiting examples of hardware systems to carry out the invention are presented in FIGS. 5 and 6.

FIG. 4 shows a hardware implementation that can be deployed on a single server 501, where the single server can be laptop or desktop computer. The server 501 serves as the trusted server 101 described in FIG. 1. Users 505 of the server 501 can communicate with the server 501. Communication can be accomplished via the internet or by other network means; an internet connection is not required to practice the invention. In certain embodiments, users 505 can communicate with the server 501 using widely-available HTML viewers.

Users 505 first communicate with a security module 510 implemented on the server 501. The security module 510 can be a form-based authentication where users are verified using a username and password combination. A username and password combination will identify the user 510 as a physician user, diagnostic test provider, patient user, payer party user or rights holder user and implement the proper interface and related privacy rules to control access to information. Alternatively, access to the server 501 can be granted based upon the user uploading a security file containing encrypted identification information.

The server 501 implements a web server 520 that includes a user interface (UI) 425 that is presented to the user 505. The UI 525 is not limited to any particular software, standard or language. In certain embodiments, the UI 525 can be based on a JavaScript Library including HTML5, css3.0 and a robust JavaScript Library Toolkit that supports Web 2.0 standards. The UI 425 can therefore be a graphical interface that can be intuitively operated by the user 405. As described, one or more parser algorithm tools or search engines 530 can be implemented on the server 401 to parse genetic data. In one embodiment, the parser algorithm tool 530 can be BioJava (http://www.biojava.org/wiki/Main Page), which has the advantage of being readily implemented with a JAVA-based web server. In another embodiment, the parser algorithm tool 530 can be BioParser (http://bioinformatics.tgen.org/brunit/software/bioparser). Since BioParser is written in PERL, a wrapper is required to implement BioParser with a JAVA-based web server, for example, JPL or JNI. The notification server 140 can be implemented with an included JAVA mail client 535 to send notifications to users 505 even when a user 505 is not logged onto the server 501. The mail client 535 can also implement the payment facility 160 where a payer party user and/or rights holder user can be notified of the obligation for a payment to be made in a blinded fashion.

The patient records database 105, the proprietary records database 110 and the payment log or database 150 can be accommodated on a storage device 540. The databases stored on storage device 540 are not limited to any particular structure. In some embodiments, the patient records database 105, proprietary records database 110 and the payment log or database 150 are structured to be assessable and/or queryable using structured query language (SQL) used to maintain relational databases. In one embodiment, the databases use a relational database management system such as the Oracle 8i™ product (version 8.1.7) by Oracle. In another embodiment of the databases, object-oriented database management system architecture is used.

Figure 6:
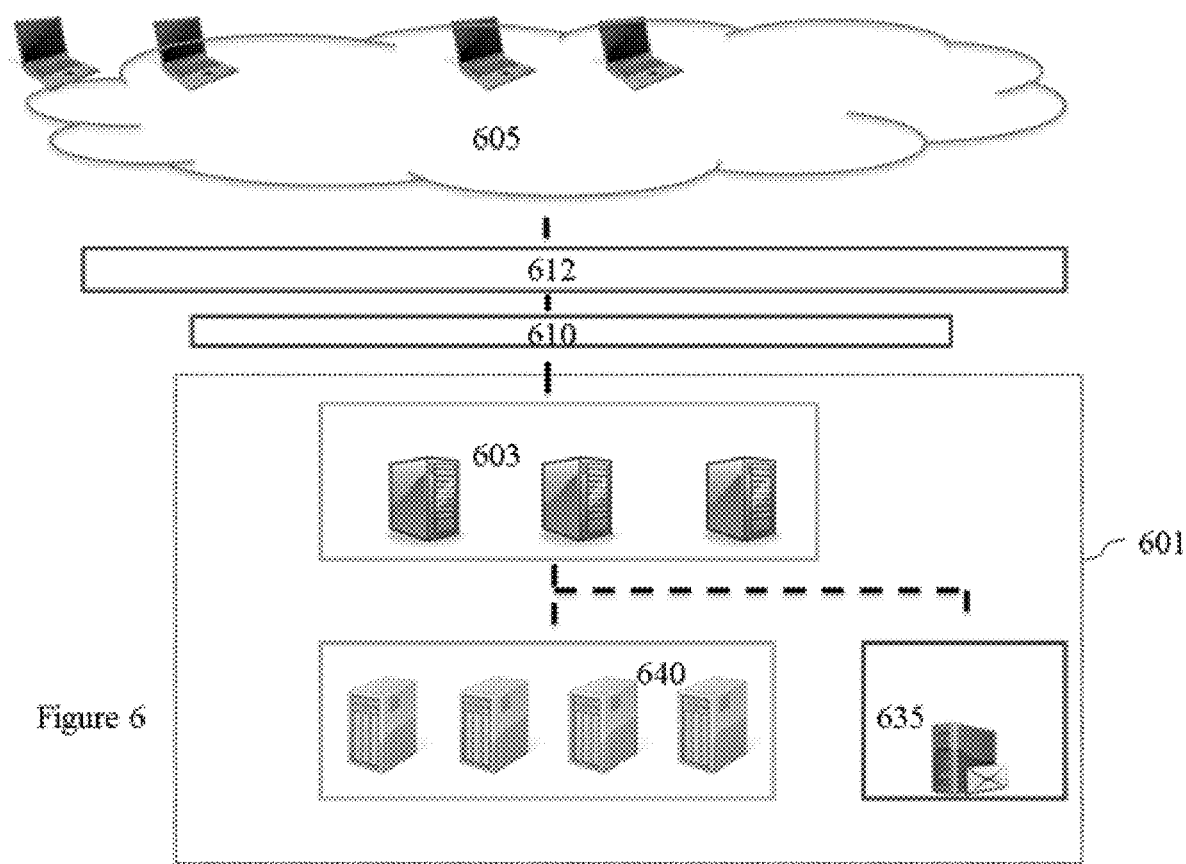
FIG. 6 shows an exemplary large-scale hardware implementation for implementing the methods described herein.

FIG. 6 shows a hardware implementation that employs several processors for a large-scale implementation. The function of the one or more processors 103 described in FIG. 1 is carried out by one or more processing units 603 that provide the computational power to implement a UI, a parser algorithm and a security module 610 and provide services to users 605 in the same manner as described above in FIG. 5. A load balancer 612 is also present to manage work flow in implementations where more than on processing unit 601 is present. The load balancer 612 divides the workload multiple processing units 601. If a fault occurs with one of the processing units 601, the load balancer 612 can automatically route requests from users 605 until the fault has been corrected.

The processing units 601 can access a storage area network (SAN) that houses the patient records database 105, the proprietary records database 110 and the payment log or database 150. A separate mail server 635 containing dedicated processor capability can be present to generate a large volume of outgoing email. The payment facility 160 can be implemented using the one or more processing units 603.

Figure 7:
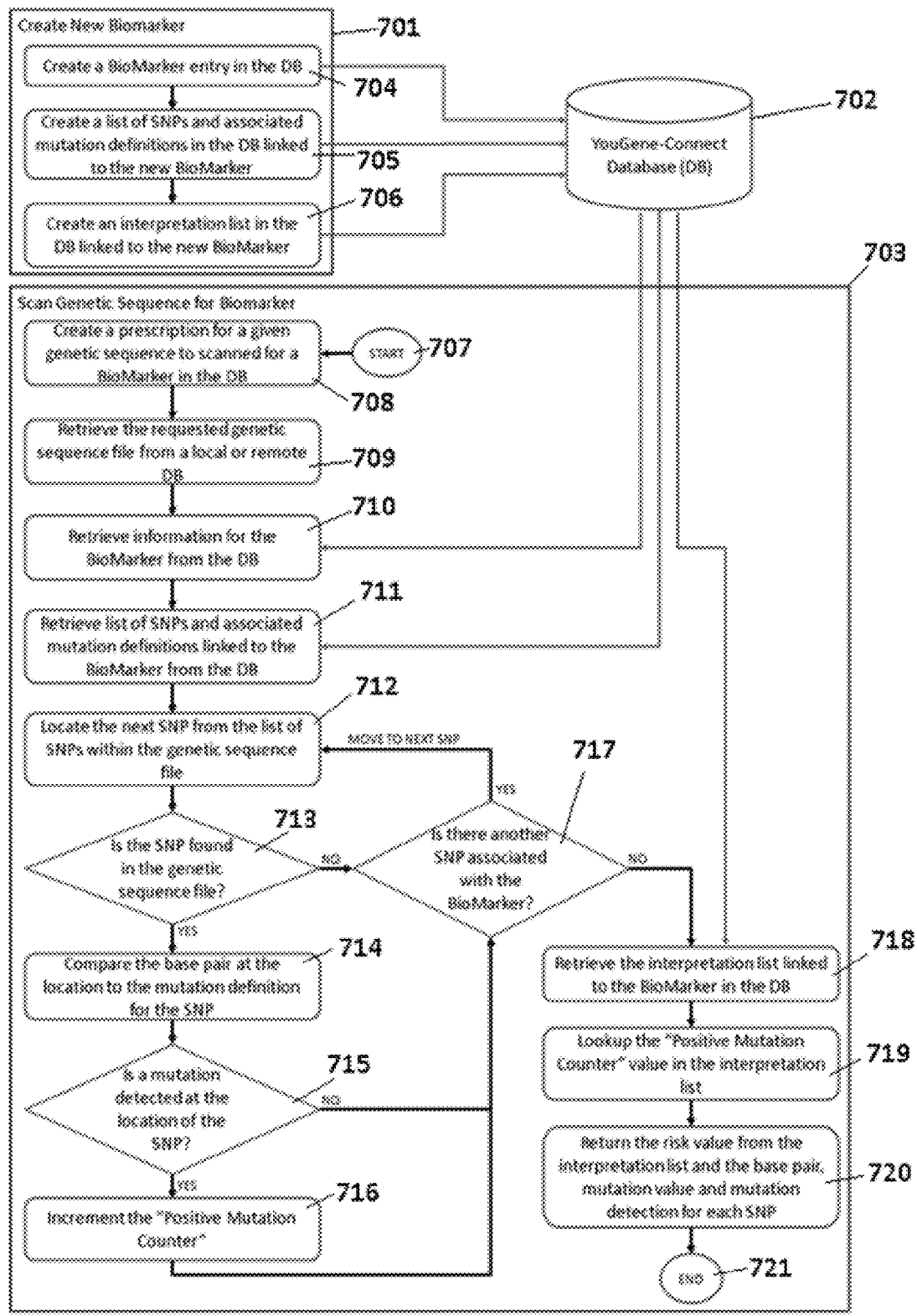
FIG. 7 shows a flow chart for the method of creating a biomarker script and conducting a scan of a genome.

The system and method for encoding a script to query the patient's genetic sequence is shown in FIG. 7. In particular, the method of creating a new biomarker script is shown in box 701 of FIG. 7.

To create a new biomarker script 701, a new biomarker entry can be created 704 in a biomarker script database 702. A list of SNPs and associated mutations that are linked to the biomarker can be created 705 in the biomarker script database 702. An interpretation list linked to the new biomarker can be created 706 in the biomarker script database 702. The list of SNPs and associated mutations can include such information as the mutation value and where to look in the sequence for the mutation. The interpretations list can include such information as risk factors based on each mutation and confidence intervals for combinations of SNP mutations found. The biomarker is able to combine various SNPs and mutations within the same genre or from multiple genes to calculate a single risk value based on this combination of multiple factors.

The biomarker scripts of the present invention confer advantages over tests that determine outcomes based on protein or enzymes. Unlike protein or enzyme levels, which can vary with time, the patient's genome is static. As a result, a patient's genome only needs to be scanned a single time. By contrast, tests that measure protein or enzyme levels may need to be repeated several times to account for changes in protein or enzyme levels. Further, once a genetic scan is completed, any biomarker can be searched in the future using the same genetic scan.

In any embodiment, the biomarker script can be the equivalent to any known enzyme or PCR based diagnostic test kit. For PCR based test kits, this can be accomplished by using the probes utilized by known diagnostic test kits as the list of SNPs in the biomarker script. For enzyme tests, the equivalence can be accomplished by determining the identity of an expression quantitative trait loci (eQTL) corresponding to the particular enzyme or enzymes. The eQTLs are the regions of the genome that cause the particular enzyme to be expressed. An enzyme based test may determine a genetic disorder by measuring the levels of the enzyme in the patient's blood. A biomarker script of the present invention can instead search for the underlying mutation in the patient's genome that causes the discrepancy in the enzyme levels. In other embodiments, the biomarker script can be different from known diagnostic test kits.

An example of a list of SNPs and mutations associated with a particular biomarker is shown in Table 1 for breast cancer. Each of the mutations shown in Table 1 corresponds to a particular location in the genome where a mutation is associated with an increased risk of breast cancer. The mutations are defined according to the location of the mutation in the genetic sequence, and which bases in the location correspond to an increased risk of the disease. The list, including the location, mutation and matching criteria can be created in the biomarker script database 702.

TABLE 1

|  | Mutation | Matching Criteria |
|---|---|---|
| BRCA1 gene SNP | | |
| rs1799950 | G | Either Position in SNP Pair |
| rs4986850 | A | Either Position in SNP Pair |
| rs2227945 | G | Either Position in SNP Pair |
| rs16942 | G | Either Position in SNP Pair |
| rs1799966 | G | Either Position in SNP Pair |
| rs766173 | G | Either Position in SNP Pair |

TABLE 1-continued

| | Mutation | Matching Criteria |
|---|---|---|
| rs144848 | G | Either Position in SNP Pair |
| rs4987117 | T | Either Position in SNP Pair |
| rs2799954 | T | Either Position in SNP Pair |
| rs11571746 | C | Either Position in SNP Pair |
| rs11571747 | C | Either Position in SNP Pair |
| rs4987047 | T | Either Position in SNP Pair |
| rs11571833 | T | Either Position in SNP Pair |
| rs1801426 | G | Either Position in SNP Pair |
| ATM gene SNP | | |
| rs3218707 | C | Either Position in SNP Pair |
| rs4987945 | G | Either Position in SNP Pair |
| rs4986761 | C | Either Position in SNP Pair |
| rs3218695 | A | Either Position in SNP Pair |
| rs1800056 | C | Either Position in SNP Pair |
| rs1800057 | G | Either Position in SNP Pair |
| rs3092856 | T | Either Position in SNP Pair |
| rs1800058 | T | Either Position in SNP Pair |
| rs1801673 | T | Either Position in SNP Pair |
| CHEK2 gene SNP | | |
| rs17879961 | C | Either Position in SNP Pair |
| TP53 | | |
| rs1042522 | G | Either Position in SNP Pair |

An example of an interpretation list for the BRCA gene is shown in Table 2. The interpretation list can determine the increase in risk of a particular disease, such as breast cancer, based on the mutations found in the patient's genetic sequence. The risk factors in Table 2 are shown as multiples representing the increase in risk due to the patient having the genetic mutations. The low and high confidence intervals represent the 95% confidence levels of the risk factors. A patient that has no mutated SNPs, by definition, has a risk factor of 1. Patients with one or more of the listed SNPs have a higher risk of developing cancer in their lifetime. A unique interpretation list for each diagnostic test available can be created in the biomarker script database 702.

TABLE 2

| | | Confidence Interval | |
|---|---|---|---|
| Number of Mutated SNPs | Risk Factor | Low | High |
| 0 | 1X | 1 | 1 |
| 1 | 1.46X | 0.89X | 2.40X |
| 2 | 1.39X | 0.86X | 2.25X |
| 3 | 1.75X | 1.09X | 2.80X |
| 4 | 1.56X | 0.95X | 2.55X |
| 5 | 1.31X | 0.76X | 2.24X |
| 6 | 1.84X | 1.04X | 3.26X |
| 7 | 2.10X | 1.06X | 4.16X |
| 8 | 4.02X | 1.56X | 10.38X |
| 9 or more | 8.04X | 1.89X | 34.26X |

In some embodiments, the list of SNPs in the biomarker script and the interpretation list can be the same as what is provided for by known or commercially available test kits. One example of such a test kit MammoPrint by Myraid Genetics. The same SNPs that are searched for with the test kit can be made part of the SNP list of the present invention. The same interpretations provided by the test kit can be made part of the interpretation list of the present invention. In this way, the encoded biomarker script would be the equivalent of the known test kits.

Once the biomarker entry has been created with the list of SNPs and interpretations, the system scan a sequence for a biomarker, as shown in box 703 in FIG. 7. At the start of the scan 707 a prescription for a particular genetic sequence to be scanned is created 708. Based on the prescription, the system can retrieve the particular genetic sequence from a genetic sequences database 709. The genetic sequences database can in some embodiments be a remote database, separate from the biomarker script database 702. In other embodiments, the genetic sequences database can be local to the biomarker script database 702. In some embodiments, either one of the genetic sequences database or biomarker script database 702 can be embedded within the other.

The biomarker information can be retrieved 710 from the biomarker script database 702. The list of SNPs and associated mutations can be retrieved 711 from the biomarker script database 702. Using the list of SNPs, the system can scan the genetic sequence and locate the position of one of the SNPs 712. The system can determine if the SNP is found in the genetic sequence file 713. If the SNP is found in the genetic sequence file, the system can then compare the base pair at the particular location in the sequence to the mutation definition in the list of mutations 714. The system determines if a mutation is detected at the particular location 715, and if so increments a positive mutation counter 716. The system next determines if there are any other SNPs associated with the biomarker 717. If there are any more SNPs associated with the biomarker, the system again determines if the next SNP is found in the genetic sequence file 713. If any mutation is not detected, or if any SNP is not found in the genetic sequence file, the system can skip to step 717 without incrementing the positive mutation counter, and can determine if there are any other SNPs associated with the biomarker.

Once all SNPs associated with a biomarker have been searched in the genetic sequence, the system can retrieve the interpretation list 718 from the biomarker script database 702. The system can look up the positive mutation counter value determined in step 716 and find the corresponding risk value in the interpretation list 719. The results can be returned 720 and the process ended 721. In any embodiment, the results can include one or both of the risk factor and the mutations detected at each SNP.

A physician can create a prescription using the secure log-in as explained above. A screenshot step of creating a prescription is shown in FIG. 8. The physician can enter in a physician ID 801 which will allow the physician to access the information in a particular sequence. The physician can also enter a patient ID 802, which identifies the particular sequence to be tested. The biomarker ID 803 can be entered, which determines which biomarker script the system will use. Finally, the physician can enter whether this is a new or tumor specific scan 804. This informs the system whether a specific tumor is being scanned, which can determine which SNPs are of particular value. In some embodiments, the prescription can be created automatically from the patient's electronic medical records. This can be done using a third party application interface to automatically create the prescription in the system.

After the physician creates the prescription, the system can automatically locate the patient's genetic sequence and the necessary biomarker script. Upon retrieval of the sequence and biomarker script, the system can automatically scan the patient's sequence as explained in FIG. 7. A screenshot of the system during the retrieval and scanning processes is shown in FIG. 9. This screen can notify the physician that the requested patient sequence is on file in the database and that the test is being or will be run. Depending on the capacity of the system, the scanning process can be completed in less than two seconds.

Figure 10:
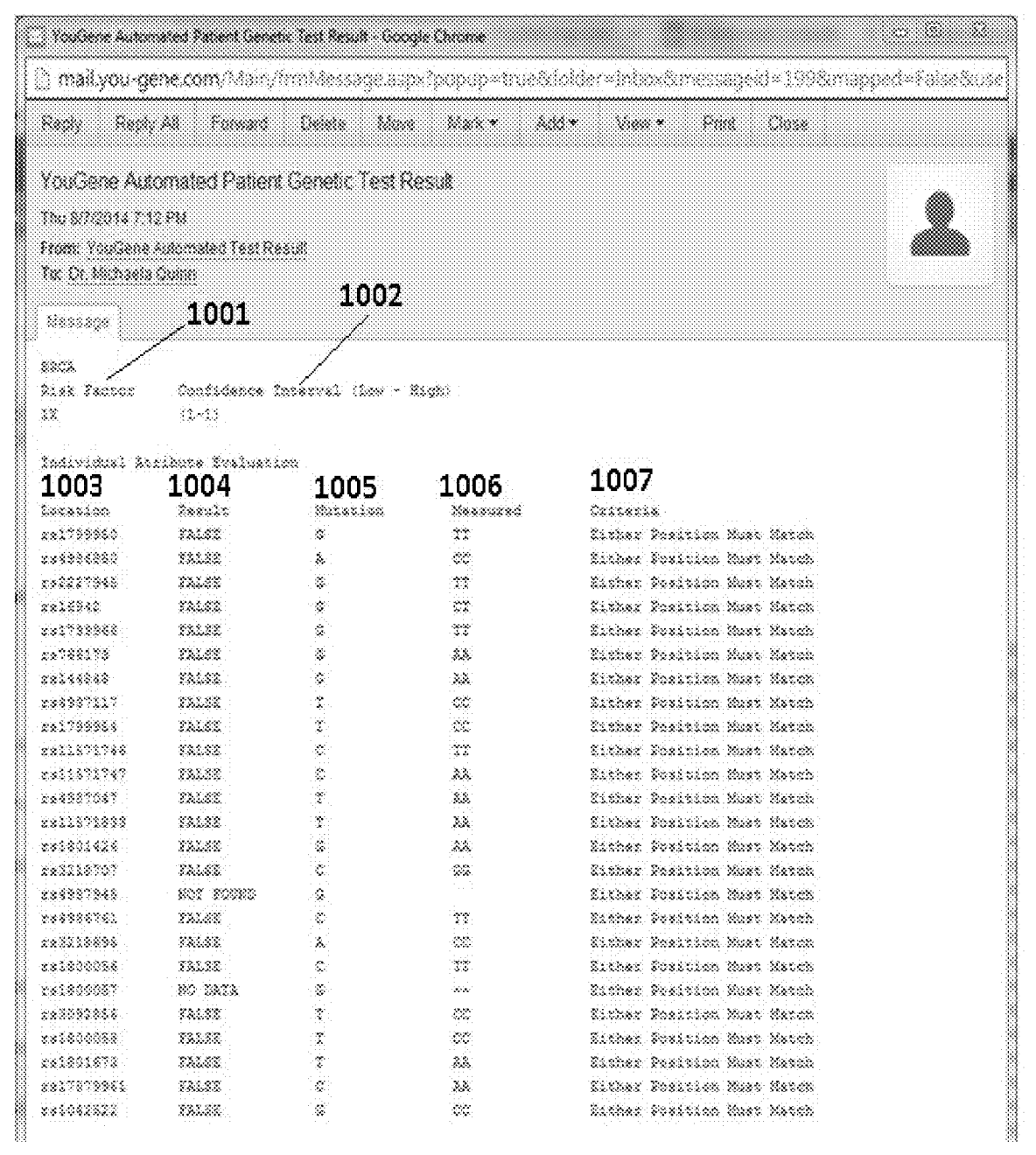

FIG. 10 shows a screenshot of the results output after running the scan. The test results can be provided to the prescribing physician or to the patient. The output includes the overall risk factor 1001 and the 95% confidence intervals 1002. In any embodiment, the output can also include the particular locations searched 1003, the result of the search at those locations 1004, the mutation 1005, the genotype found 1006, and the criteria to be counted as a mutation 1007. It will be understood that not all of the information provided in FIG. 10 needs to be included, and that any output providing the results of the genetic test are within the scope of the invention.

As can be seen in FIG. 10, the particular sample genetic sequence did not test positive for any of the mutations shown in Table 1. As such, the patient's risk factor for breast cancer based on the test is 1x, by definition.

An example of an output provided for a patient that does test positive for some mutations is shown in FIG. 11. As can be seen, the patient tested positive at the positions rs16942 1101, rs766173 1002, and rs144848 1003. Because three positive mutations were found, the system reported the risk factor from Table 2 corresponding to three mutations, and returned that the patient had a breast cancer risk factor of 1.75x with 95% confidence intervals between 1.09x and 2.80x.

In any embodiment, the system may also determine any proprietary rights in the biomarkers used. It can automatically notify the rights holders and payer parties of the test, and account for payment to the rights holders, as explained in FIGS. 1-6. In any embodiment, the system may also control access to information or access to any database, application or server as outlined above in order to protect privacy.

It will be apparent to one skilled in the art that various combinations and/or modifications and variations can be made in the system depending upon the specific needs for operation. Moreover features illustrated or described as being part of one embodiment may be used on another embodiment to yield a still further embodiment.

We claim:

1. A method for conducting genetic testing, comprising:
    scanning a genome or portion of a genome of a patient with a remote client containing an interpretations list to determine the presence of one or more genetic mutations associated with a disease; and providing a risk factor corresponding to a determination of the presence of the one or more genetic mutations;
    accessing a proprietary records database containing records of proprietary biomarkers and rights holders of the proprietary biomarkers;
    determining the presence of a proprietary biomarker in the genome or portion of the genome of the patient;
    automatically forwarding information obtained from scanning the genome or portion of the genome to determine the presence of the proprietary biomarker to one or more of a payer party user and a rights holder user associated with the proprietary biomarker used; and
    accounting for a payment or escrow between a payer party user and a rights holder user of the proprietary biomarker used by the scan;
    wherein the genome or portion of the genome is stored in a storage area network collocated with the remote client; wherein the storage area network is configured to receive the genome or portion of a genome of multiple patients from multiple sources;
    wherein the interpretations list contains a risk factor for the disease based on the one or more genetic mutations;
    wherein the risk factor is used in diagnosis of at least one condition or disease;
    wherein the information forwarded to the rights holder user does not contain patient identification information of the patient; and
    wherein the step of scanning a genome or portion of a genome of a patient to determine the presence of the one or more genetic mutations:
        (a) retrieving a list of genetic mutations from the interpretations list;
        (b) scanning the genome or portion of a genome of the patient for each of the one or more genetic mutations in the interpretations list; and
        (c) determining a number of mutations present in the genome or portion of a genome.

2. The method of claim 1, wherein the step of scanning a genome or portion of a genome of a patient to determine the presence of the one or more genetic mutations further comprises:
    obtaining a prescription for a genome or portion of a genome of the patient, the prescription comprising a patient identifier, a genetic sequence identifier and a biomarker identifier.

3. The method of claim 1, wherein the interpretations list provides a risk factor based on a number of mutations found corresponding to mutation definitions.

4. The method of claim 1, further comprising the step of counting a number of the one or more genetic mutations found in the genome or portion of a genome.

5. The method of claim 1, further comprising providing a list of each mutation found in the genome or portion of a genome corresponding to a mutation definition.

6. The method of claim 2, wherein the step of obtaining a prescription for a genome or portion of a genome comprises obtaining the prescription through electronic medical records of a patient.

7. The method of claim 1, further comprising the step of receiving a biomarker entry into the interpretations list; the biomarker entry comprising at least one genetic mutation and a risk score for a disease based on the at least one genetic mutation.

8. The method of claim 1, further comprising the step of locating the genome or portion of the genome for a patient in the storage area network based on a patient identification number associated with the genome or portion of the genome.

9. A system for conducting a genetic test comprising;
    an interpretations list in communication with a remote client, wherein the interpretations list contains a risk factor for one or more diseases based on one or more genetic mutations;
    a patient records database comprising patient identification information for at least one patient, and a genome or portion of a genome for the at least one patient;
    a proprietary records database containing information regarding rights holders to one or more proprietary biomarkers;
    a payment facility configured to account for a payment from a payer party to the rights holders if any of the one or more genetic mutations is a proprietary biomarker, wherein the payment facility forwards information regarding the presence of a proprietary biomarker in the genome or portion of the genome of the patient to the payer party and/or the rights holders;

wherein the patient records database is in a storage area network collocated with the remote client; wherein the storage area network is configured to receive the genome or portion of a genome of multiple patients from multiple sources;

wherein the remote client is programmed to scan the genome or portion of a genome of a patient to determine the presence of the one or more genetic mutations by:

retrieving the one or more genetic mutations from the interpretations list;

scanning the genome or portion of a genome of the patient for each of the one or more genetic mutations; and determining a number of mutations present in the genome or portion of a genome wherein the risk factor is used in diagnosis of at least one condition or disease.

10. The system of claim 9, further including a privacy facilitating system that can set rules to control user access to any database accessible by the privacy facilitating system or any record generated by the privacy facilitating system.

11. The system of claim 9, wherein the system is configured to obtain a prescription for a genetic test and the remote client is programmed to receive the prescription and to scan the genome or portion of the genome based on the prescription for a genetic test.

12. The system of claim 11, wherein the system is configured to receive the prescription for a genetic test from electronic health records.

13. The system of claim 9, wherein the system is programmed to receive a biomarker entry comprising at least one genetic mutation and a risk score based on the at least one genetic mutation.

14. The system of claim 13, wherein the system is programmed to include biomarker entry in the interpretations list.

15. The system of claim 9, wherein the storage area network comprises genomes or portions of genomes of one or more patients and a patient identification number for each genome or portion of a genome.

* * * * *